US006682724B2

(12) United States Patent
Mohseni et al.

(10) Patent No.: US 6,682,724 B2
(45) Date of Patent: *Jan. 27, 2004

(54) SONIC METHOD OF ENHANCING CHEMICAL REACTIONS TO PROVIDE UNIFORM, NON-AGGLOMERATED PARTICLES

(75) Inventors: Saeed H. Mohseni, Fairport, NY (US); John J. Jardas, Rochester, NY (US)

(73) Assignee: Arch Chemcials, Inc., Norwalk, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 10/176,180

(22) Filed: Jun. 20, 2002

(65) Prior Publication Data
US 2002/0197282 A1 Dec. 26, 2002

Related U.S. Application Data

(62) Division of application No. 09/256,969, filed on Feb. 23, 1999, now Pat. No. 6,465,015.

(51) Int. Cl.[7] .............................. A61K 7/06; A61K 7/09; A61K 9/14
(52) U.S. Cl. ..................... 424/70.1; 424/70.4; 424/489; 424/490; 424/491
(58) Field of Search ................. 424/70.1, 70.4, 424/489, 490, 491; 264/115, 117, 118

(56) References Cited

U.S. PATENT DOCUMENTS

| 2,786,847 A | 3/1957 | Cislak ..................... 260/294.8 |
| 2,809,971 A | 10/1957 | Bernstein et al. .......... 260/260 |
| 3,264,242 A | 8/1966 | Teot ......................... 260/29.6 |
| 3,589,999 A | 6/1971 | McRae et al. ............... 210/28 |
| 3,590,035 A | 6/1971 | Damico .................... 262/290 |
| 3,634,272 A | 1/1972 | Valenta et al. ............. 252/153 |

(List continued on next page.)

FOREIGN PATENT DOCUMENTS

| CH | 683592 A5 | 4/1994 | ............ A61K/9/52 |
| EP | 0 093 541 | * 9/1983 | |
| WO | WO 0 034 385 A2 | 2/1980 | ......... C07D/213/89 |
| WO | WO 0 093 541 A2 | 11/1983 | ............ A61K/7/06 |
| WO | WO 0 295 903 A2 | 12/1988 | ............ A61K/7/06 |

OTHER PUBLICATIONS

Mason, T J; "The Uses of Ultrasound in Chemistry", pp. 58–59 and 132–139 (1990).*
Luche, J L; "Synthetic Organic Sonochemistry", pp. 326–327 (1998).*
Mason, T J: "The Uses of Ultrasound in Chemistry", pp. 58–59 and 132–139 (1990).
Crum, Larry K: Chemical Engineering, pp. 37, 39 and 41 (Oct. 1992).
Luche, Jean–Louis: "Synthetic Organic Sonochemistry", pp. 326–327 (1998).

Primary Examiner—Thurman K. Page
Assistant Examiner—S. Tran
(74) Attorney, Agent, or Firm—Dale Lynn Carlson Wiggin & Dana LLP

(57) ABSTRACT

A method for making a suspension, dispersion or emulsion of non-agglomerated particles comprising forming particles in a liquid medium, wherein sonic energy is applied to the liquid medium at the point of contact of the reactants during the particle forming step to produce the suspension, dispersion or emulsion of non-agglomerated particles. The invention is also directed to a method for making a suspension of non-agglomerated pyrithione salt particles, comprising the steps of forming pyrithione salt particles in a liquid medium, wherein sonic energy is applied to the liquid medium during the forming step to produce the suspension of non-agglomerated pyrithione salt particles.

2 Claims, 3 Drawing Sheets

U.S. PATENT DOCUMENTS

| | | | |
|---|---|---|---|
| 3,773,770 A | 11/1973 | Damico | 260/290 |
| 3,945,437 A | 3/1976 | Chiu et al. | 166/305 |
| 4,168,295 A | 9/1979 | Sawyer | 422/111 |
| 4,466,870 A | 8/1984 | Boudjouk et al. | 204/156 |
| 4,576,688 A | 3/1986 | David | 204/159.62 |
| 4,670,430 A * | 6/1987 | Imamura et al. | 514/188 |
| 4,898,621 A | 2/1990 | Pruehs et al. | 134/25.5 |
| 4,919,804 A | 4/1990 | Dorsey et al. | 210/198.2 |
| 4,925,587 A | 5/1990 | Schenker et al. | 252/174.22 |
| 5,108,654 A | 4/1992 | Ragaomo | 252/314 |
| 5,198,122 A | 3/1993 | Roszalka et al. | 210/748 |
| 5,658,534 A | 8/1997 | Desborough et al. | 422/128 |
| 5,688,981 A | 11/1997 | Nonomura | 556/116 |
| 5,762,650 A | 6/1998 | Ruggiero et al. | 8/490 |
| 6,017,562 A * | 1/2000 | Kaufman et al. | 424/489 |
| 6,017,936 A * | 1/2000 | Polson et al. | 514/345 |
| 6,143,037 A | 11/2000 | Goldstein et al. | 623/66 |
| 6,432,432 B1 * | 8/2002 | Mohseni et al. | 424/405 |

* cited by examiner

US 6,682,724 B2

SONIC METHOD OF ENHANCING CHEMICAL REACTIONS TO PROVIDE UNIFORM, NON-AGGLOMERATED PARTICLES

CROSS-REFERENCE TO RELATED APPLICATION

This application is a division of U.S. patent application Ser. No. 09/256,969, filed Feb. 23, 1999 now U.S. Pat. No. 6,465,015, the disclosure of which application is incorporated by reference in its entirety herein.

BACKGROUND OF THE INVENTION

1. Field of the Invention

The invention relates generally to sonic (e.g., ultrasound) methods of making suspensions of uniform, non-agglomerated particles, and more particularly to methods for making a chemical reaction product that is a suspension, dispersion or emulsion of non-agglomerated, uniformly shaped particles at high production rates of up to 100 gallons per minute or higher. When the chemical reaction is effected in the presence of sonic energy, in close proximity to the point of contact of the reactants in the reactor, intimate mixing of the reactants is achieved to facilitate a more complete, uniform reaction than is achieved using conventional bladed-mixer systems.

2. Description of the Prior Art

Suspensions of very small, solid or liquid particles are useful in many applications, including personal care products (e.g., shampoos, soaps, etc.), cleaning products, paints, coatings, foodstuffs, fertilizers, pool chemicals, and the like. Generally, a well-dispersed suspension or emulsion of uniformly sized, non-agglomerated particles is desired because such suspensions provide a large and uniform surface area which results in improved performance of these products. Accordingly, much effort has been expended to develop methods to prepare well-dispersed suspensions of uniformly sized, non-agglomerated small particles, particularly such particles in the range of from submicron size to a few microns in size. One method involves using chemistry to control the particles' size and/or shape during their formation in the chemical reaction employed to produce the particles. Another method uses physical mixing of the particles, during or after their production in a liquid suspension or emulsion, or grinding of the particles that are formed, to provide a desired size or shape. As another alternative, a combination of these methods has been investigated heretofore.

Chemical methods for control of particle size and/or shape generally focus upon manipulating the parameters of the precipitation reaction under which the particles are formed. For example, the use of additives, such as surfactants, to the particle-forming precipitation reaction mixture is suitably utilized to provide a suspension of specific shaped particles having a particle size distribution within the range of from about 0.5 to 30 microns (micrometers or "$\mu$m") in size. However, it is difficult to achieve suspensions of small solid or liquid particles having an "essentially uniform size and shape" using surfactant additives alone. The term "essentially uniform size" as used herein, is intended to designate that the particles referred to have dimensions that do not vary by more than twenty percent, preferably not more than ten percent, between individual particles in the particulate product. The term "essentially uniform shape", as used herein, is intended to designate that the particles referred to have essentially identical shapes, i.e., that the shapes of the particles within a given particle distribution are essentially identical. More specifically, if the particles in a distribution referred to as "essentially uniform in shape" are largely hexagonal in shape, then at least 80%, preferably at least 90%, of the particles in this distribution would be hexagonal in shape.

By changing other reaction parameters, such as by decreasing the temperature of the precipitation reaction, in combination with the use of a surfactant additive, it is possible to produce suspensions of solid particles having dimensions in a particle size range of from 0.5 to 5 $\mu$m. However, this range of size distribution is still greater than might otherwise be desired. Accordingly, there is a continuing need in the dispersions, suspensions and emulsions manufacturing community for particulate products having a particle distribution that is essentially uniform in size and shape. The present invention provides one answer to that need.

Heretofore, various mixing and/or grinding techniques have been employed in an effort to further reduce particle size without impairing the configuration or shape of the particle. Generally, conventional mixing procedures utilize a blade-type mixing apparatus such as a blender. The blade portion of the apparatus rotates at a specified rate to generate shear forces that physically reduce the sizes of the particles. Unfortunately, however, these bladed mixers pose a number of problems in the manufacture of suspensions of small particles, such as biocides. For example, bladed mixers tend to pull air into the reaction medium, and the entering air can cause unwanted foaming or thickening of the suspension. Blade-type mixers also have the undesirable effect of providing non-uniform mixing at various points within the reaction chamber. This result is believed to be attributable to the fact that the amount of shear force generated at the edge of the blade is greater than elsewhere in the reaction vessel, such as the surface, bottom or sides of the reactor vessel. Needless to say, differing applied shear forces at different points within the reactor vessel can adversely influence the chemistry of particle formation.

In view of these problems and disadvantages, it is difficult to prepare a well-dispersed suspension of uniformly sized and shaped, non-agglomerated particles using a bladed mixing approach. Nonetheless, in the production of solid biocides, bladed mixing, grinding, and centrifugation have found widespread use. For example, the biocides iodopropargylbuylcarbamate (so-called "IPBC") and pyrithione are typically produced using bladed mixing or centrifugation, and the resulting product is generally size- and shape-determined by virtue of the reactants and reaction parameters that are employed. In the past, biocide manufacturers have used grinding to further reduce the size, or alter the shape, vis-à-vis the size and shape of the particles that result from the reaction itself. Unfortunately, however, grinding tends to have an adverse effect on the desired uniformity of shape of the biocide particles, as discussed in more detail hereinbelow.

Specific examples of useful pyrithione biocides include polyvalent metal salts of pyrithione (also known as 1-hydroxy-2-pyridinethione; 2-pyridinethiol-1-oxide; 2-pyridinethione; 2-mercaptopyridine-N-oxide; pyridinethione; and pyridinethione-N-oxide). These pyrithiones have enjoyed widespread application as fungicides and bactericides in paints and personal care products such as anti-dandruff shampoos. The polyvalent metal salts of pyrithione are solids that are only sparingly soluble in water and include magnesium pyrithione, barium pyrithione, bismuth pyrithione, strontium pyrithione, copper pyrithione, zinc pyrithione, cadmium pyrithione, and zirconium pyrithione. The most widely used divalent pyrithione salts are zinc pyrithione and copper pyrithione. Both zinc and copper pyrithione are useful as antimicrobial agents active against gram-positive and negative bacteria, fungi, and yeasts. Zinc pyrithione is used as an antidandruff component in shampoos, while technical suspensions of zinc pyrithione and/or copper pyrithione are used as preservatives in paints and polymers. Synthesis of polyvalent pyrithione salts are described in U.S. Pat. No. 2,809,971 to Berstein et al. Other patents disclosing similar compounds and processes for making them include U.S. Pat. Nos. 2,786,847; 3,589,999; 3,590,035; and 3,773,770.

The size limitations on pyrithione salt particle production made by conventional bladed mixing methodology demonstrate the drawbacks of using such processing. Illustratively, known methods for producing insoluble polyvalent salts of pyrithione typically result in solid particles having an average size greater than one micrometer ($\mu$m). However, as discussed above, smaller particles of pyrithione salts (i.e., less than one micron in size) are often desired because they more easily form suspensions and provide a larger surface area for enhanced biocidal activity. In addition, smaller particles, particularly in the low submicron range (e.g., below about 0.1 or 0.2 $\mu$m), may be transparent to light, and thus could provide the opportunity to manufacture "clear" products, such as clear shampoos and soaps, that are popular in the marketplace today.

Smaller particles of pyrithione salts are usually generated by a separate mechanical manipulation step (e.g., grinding or crushing) on larger particles or crystals that are made by conventional processes. For example, European Patent Application No. 70046 describes preparation of zinc pyrithione using organic solvents. This process results in production of large crystals of zinc pyrithione that are easily isolated by filtration. A separate, optional grinding step is used to grind the large crystals and produce zinc pyrithione particles of smaller size. U.S. Pat. No. 4,670,430 describes a process of making zinc pyrithione particles with a median size of about 0.2 $\mu$m by grinding larger particles of zinc pyrithione.

As an alternative to grinding, sonication technology has been used to break up large solid or liquid particles into smaller ones. To date, however, this technology has not been utilized to enhance commercial chemical reactions, to the knowledge of the present inventors, for a variety of reasons, such as scale-up problems discussed below. Nevertheless, the recent technical journal literature provides laboratory-scale data suggesting that sonication holds promise for facilitating high product yield from chemical reactions under mild reaction conditions while promoting a short reaction time. The facilitation of chemical reactions using sonication in industry could provide a major commercial advantage, such as in the manufacture of biocides such as zinc pyrithione or IPBC, both in terms of enhanced product throughput and in terms of minimization of product damage by using mild processing conditions.

Classic applications of sonication for commercial purposes have included "physical" treatments, such as cleaning, drilling, emulsification promotion, soldering, sonar detection, medical therapy, and welding. Ultrasonic sound waves have also been used commercially to analyze and evaluate the physical and chemical properties of materials, such as density, porosity, viscosity, and chemical composition.

Another field of technology has claimed attention recently; termed "sonochemistry", whereby ultrasound has been applied to mediate laboratory-scale organic synthesis reactions, as documented in Jean-Louis Luche's treatise "Synthetic Organic Sonochemistry" (Plenum Publishing Corporation, 1998). Challenges are faced, however, in efforts to scale-up such laboratory sonochemical methods, as described at page 326 of Luche's text wherein the states that "initial steps for the successful industrial set-up of sonochemical procedure are the geometrical problems (reactor design) associated with mapping and solution measurements". In a similar vein, a technical journal article by Frerich J. Keil and Sascha Daehnke published in the Hungarian Journal of Industrial Chemistry, vol. 25, no. 1, pp. 71–80 (1997) points out scale-up issues based upon energy density distribution and cavitation bubble calculations in the reactor. In the face of these scale-up issues and problems, sonochemical methodology has not been applied to its full commercial advantage heretofore, to the knowledge of the present inventors.

In view of the above, there is clearly a need in industry, that has not been satisfied to date using sonochemical methodology, for a commercially utilizable method for rapidly preparing a suspension, dispersion, or emulsion of non-agglomerated particles of a desired size and shape. Ideally, such a method would produce particles of an essentially uniform size and shape under mild reaction conditions, while avoiding the harsh shear conditions associated with bladed mixers and grinding machines. The present invention provides one answer to this need.

SUMMARY OF THE INVENTION

In one aspect, the invention is directed to an improved method for making a suspension, emulsion or dispersion of non-agglomerated solid or liquid particles, comprising the step of forming the particles by a chemical reaction of at least two reactants in a liquid medium in the presence of sonic energy, wherein the improvement comprises applying said sonic energy to the liquid medium at the point of contact of the reactants with each other, thereby causing intimate mixing of the reactants and an associated rapid completion of the reaction to produce a desired product while minimizing or reducing the risk of forming unwanted byproduct, said desired product being in the form of said suspension, emulsion or dispersion of non-agglomerated particles having an essentially uniform size and shape.

In another aspect, the present invention relates to a continuous method of making a suspension, emulsion or dispersion of non-agglomerated solid or liquid particles on a commercial scale, said method comprising continuously forming the particles by a transchelation reaction of at least two reactants by contacting said reactants at a point of contact, and applying sonic energy at said point of contact in order to cause intimate mixing and facilitate rapid transchelation at said point of contact, thereby producing a desired product while minimizing or reducing unwanted byproduct production, said desired product being in the form of said suspension, emulsion or dispersion of non-agglomerated particles resulting from said transchelation.

In another aspect, the invention is directed to a method for making a suspension of non-agglomerated pyrithione salt particles by forming pyrithione salt particles in a liquid medium by a transchelation reaction of at least two reactants, wherein sonic energy is applied to the liquid medium during the forming step at the point of contact of said reactants in order to produce the suspension of non-agglomerated pyrithione salt particles.

In yet another aspect, the invention is directed to a method for making a suspension of non-agglomerated particles of pyrithione salts, comprising the step of reacting pyrithione or a water-soluble salt of pyrithione and a water-soluble polyvalent metal salt in an aqueous medium and in the presence of a dispersing additive to produce particles of pyrithione salts, wherein sonic energy is applied to the aqueous medium during the reacting step to produce the suspension of non-agglomerated pyrithione salt particles, the non-agglomerated pyrithione salt particles having a median size of from about 0.01 to about 50 microns. The "dispersing additive" is suitably a dispersant or other agent (e.g., a thickening agent such as carboxymethylcellulose, so-called "CMC") that facilitates the formation of the desired stable suspension of solid or liquid particles in the aqueous medium.

These and other aspects will become apparent upon reading the following detailed description of the invention.

BRIEF DESCRIPTION OF THE DRAWINGS

The invention will be more fully understood from the following detailed description taken in conjunction with the accompanying drawing in which.

DETAILED DESCRIPTION OF THE INVENTION

Figure 1:
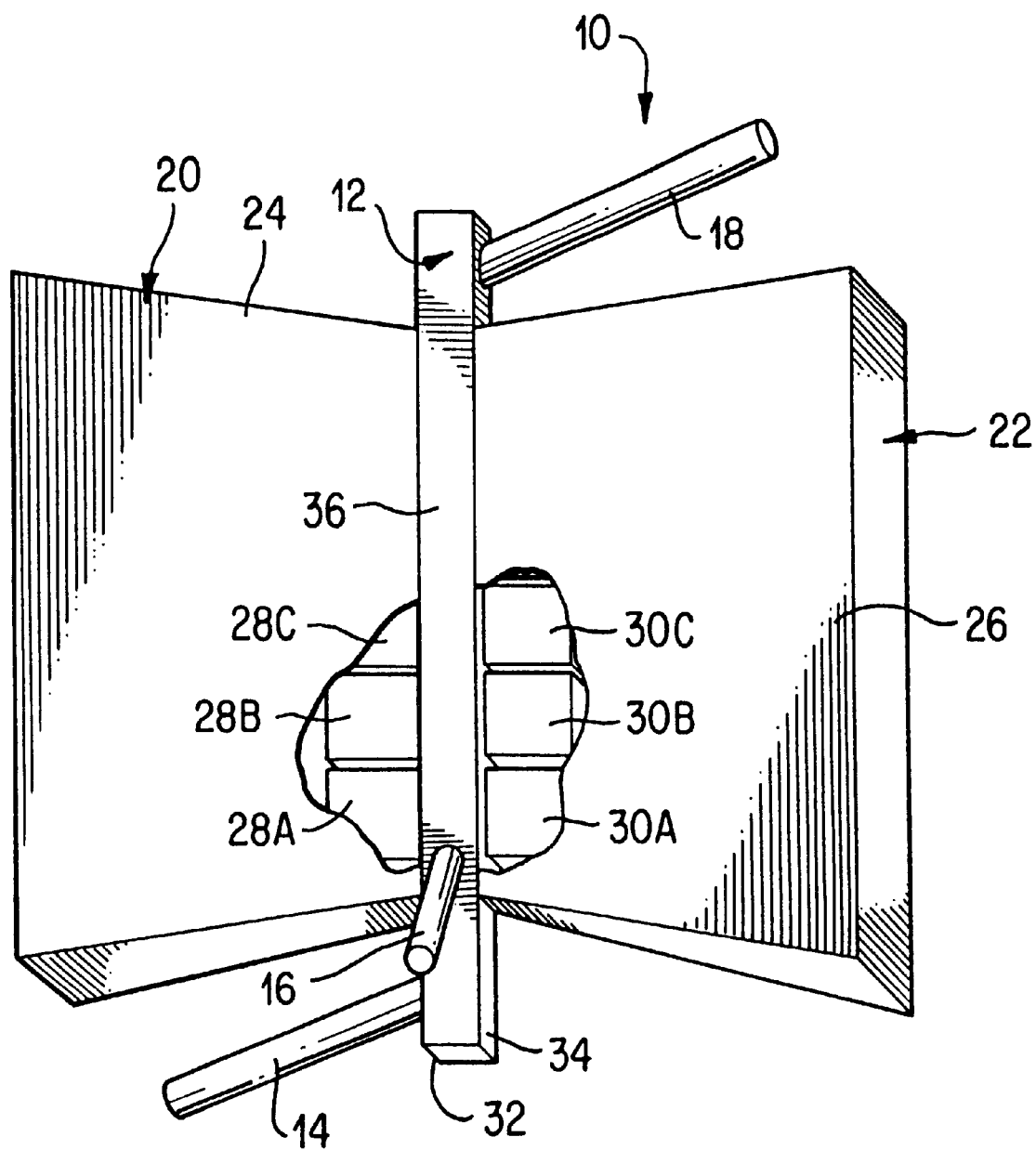
FIG. 1 is a cutaway view of a reactor design of one embodiment of the continuous process of the invention.
Figure 2:
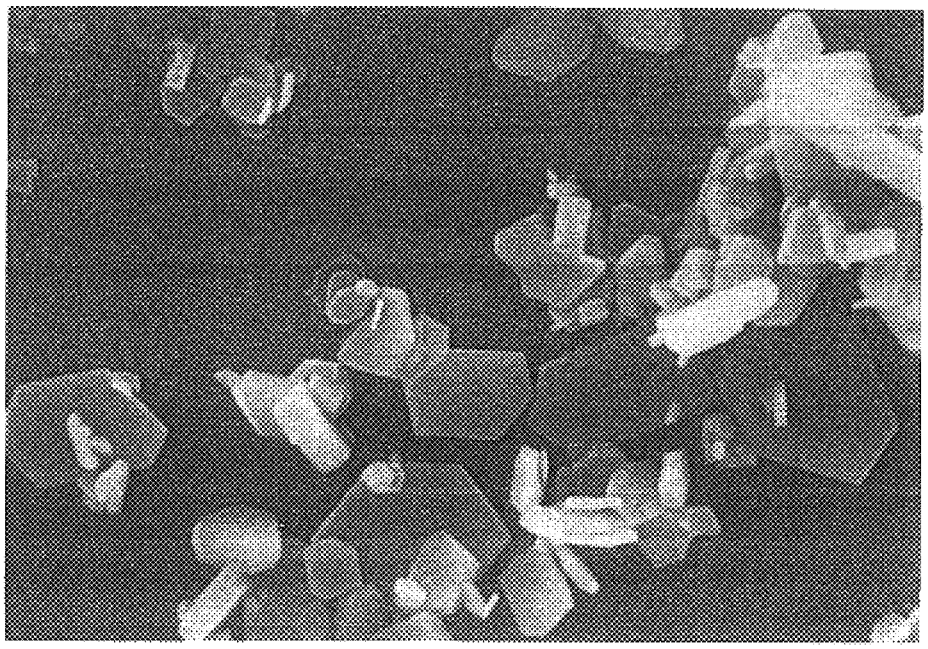
FIG. 2 is a photomicrograph at a magnification of 10,000× of hexagonal-shaped zinc pyrithione particles having sharp edges and produced in accordance with the process of the present invention.
Figure 3:
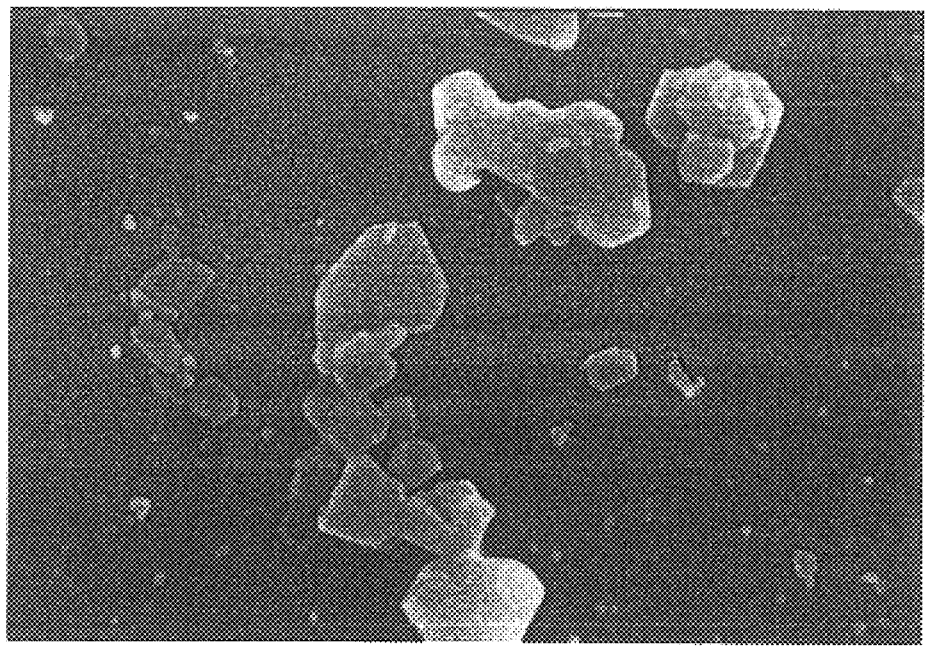
FIG. 3 is a photomicrograph at a magnification of 10,000× of irregular-shaped comparison zinc pyrithione particles having rough edges produced using conventional blade-mixing methodology.

It now has been surprisingly found, in accordance with the present invention, that a solution is provided to the long-standing problem of how to produce a well-dispersed suspension, dispersion, or emulsion of uniformly sized and shaped, non-agglomerated solid or liquid particles without employing aggressive, particle-damaging post treatment, such as grinding. The present inventors have solved this problem by utilizing a sonication step as a replacement to the conventional mixing and/or grinding steps in the particle production processes of the prior art. The method of the invention may also be used as a general method to rapidly form crystals or small solid or liquid particles of any compound from one or more reactants. The method of the invention may be practiced in either a single batch or a continuous mode. The method of the invention, when practiced in a continuous operation mode can allow for higher throughput than conventional batch processes. In other words, the present invention provides a lower cost method by which a greater quantity of particles can be manufactured in a shorter amount of time using the method of the invention, as compared to prior, batch processes. The high throughput of the invention permits increased efficiency, decreased cost, and greater productivity, advantageously by continuous processing, in a production plant.

Although the invention suitably employs any of a variety of sound waves to effect the desired sonication, energy in the ultrasound spectrum is particularly advantageous. Alternatively, the radio wave spectra are suitably employed to provide the desired energy to facilitate intimate mixing at the point of contact of the reactants.

Although the invention is suitably employed in the production of liquid dispersions of solid biocides, it is suitable for use in a variety of other applications, such as emulsion polymerization.

In one embodiment, the uniform suspension of non-agglomerated particles are pyrithione salt particles that are particularly useful in personal care products such as soaps, shampoos, and the like; paints; coatings; fertilizers; pool chemicals, or any other application where a uniform population of small particles or crystals is desired. The pyrithione salt particles made by the method of the invention are useful as antidandruff reagents in shampoos due to the uniform nature of mixing achieved by sonication, and the highly dispersed nature of the particles made by the method of the invention.

The term "sonic energy" is broadly intended by the present inventors to encompass sound waves in the audio sound spectrum, infrasound spectrum, and ultrasound spectrum, preferably in the frequency range of from 20 Hz to 900,000 Hz (900 kHz) 250,000 Hz (250 kHz) with power levels in the range from about 20 to about 5000 watts, more preferably 100 to 1000 watts, most preferably 250 to 750 watts, and decibel (dB) levels from about 10 dB to about 180 dB, preferably 50 to 100 dB, most preferably 65 to 85 dB. The term "sonication", as used herein, refers to application of sonic energy.

As used herein, the term "water-soluble salts of pyrithione" or "water-soluble pyrithione salts" include those salts of pyrithione in which the hydrogen atom of the thiol group is substituted with a monovalent cation. The term "water-soluble polyvalent metal salt" refers to those water-soluble salts in which the cation has a charge of +2 or greater. The terms "particles of pyrithione salts" or "pyrithione salt particles" as used herein refer to those salts of pyrithione that form precipitates and are essentially insoluble or sparingly soluble in the surrounding medium. The term "surfactant" as used herein refers to a compound that promotes uniform and maximum separation of extremely fine solid particles (i.e., colloidal size and shape).

In accordance with one embodiment of the process of the present invention, particles in a carrier are subjected to sonic energy to produce a uniform, non-agglomerated suspension of individual particles. The particles according to the invention may be from any commercial source. Alternatively, the particles may be made in situ as described in more detail below. Suitable particles include biocides such as magnesium pyrithione, barium pyrithione, bismuth pyrithione, strontium pyrithione, copper pyrithione, zinc pyrithione, cadmium pyrithione, zirconium pyrithione, iron (II) pyrithione, tin pyrithione, nickel pyrithione, cobalt pyrithione, manganese pyrithione, and combinations thereof. Other organic salts such as potassium sulfates and calcium hypochlorites may also be-prepared according to the method of the invention Generally, pyrithione salt particles are produced as a precipitate by reacting pyrithione or a water-soluble salt of pyrithione with a water-soluble salt of a selected polyvalent metal in the presence of a surfactant. Pyrithione in its acid form, or a water-soluble salt of pyrithione may be used in the reaction. Useful water soluble salts of pyrithione preferably include an ammonium ion or an alkali metal ion such as sodium. Accordingly, exemplary water soluble salts of pyrithione include sodium pyrithione, potassium pyrithione, lithium pyrithione, ammonium pyrithione, and combinations of these. The most preferred water-soluble salt of pyrithione useful in the present invention is the sodium salt (i.e., sodium pyrithione). The amount of pyrithione or water-soluble salt of pyrithione can vary over a wide range and establishing a useful amount is within the capabilities of the ordinary skilled practitioner based on the stoichiometry of the reaction and the required amount of particles that must be generated. A preferred amount of pyrithione or water-soluble pyrithione salt is from about 1% to about 40% by weight, more preferably from about 5% to about 25% by weight, and most preferably from about 12% to about 15% by weight, all percentages based on the total weight of the reaction mixture.

Exemplary water-soluble polyvalent metal salts useful in accordance with the method of the invention include example zinc salts, tin salts, cadmium salts, copper salts, zirconium salts, magnesium salts, aluminum salts, and the like. Combinations of these salts may also be employed. Useful counterions for these metals include nitrates, acetates, sulfates, halides or combinations thereof. Preferred water-soluble polyvalent metal salts include zinc chloride ($ZnCl_2$), copper chloride ($CuCl_2$), zinc acetate ($Zn(O_2CCH_3)_2$) and zinc sulfate ($ZnSO_4$). The amount of water-soluble polyvalent metal salt can vary depending on the amount of water-soluble salt of pyrithione, but is preferably in the range of from about 1 to about 70% by weight, more preferably from about 5 to about 30% by weight, and most preferably 15 to 20% by weight, all percentages based on the total weight of the reaction mixture. The molar ratio of pyrithione or water-soluble salt of pyrithione to the water-soluble polyvalent metal salt is preferred in the range from one mole of metal salt to about two moles of water-soluble pyrithione salt. A slight stoichiometric excess (e.g., 0.5 to 1 molar percent of water-soluble polyvalent metal salt by weight over pyrithione or water-soluble salt of pyrithione) helps to ensure a complete reaction, as is desired.

Useful media for the reaction include aqueous media such as water, or water in combination with one or more organic solvent(s). Useful organic solvents include alcohols, such as methanol, ethanol, amines such as diethanolamine, ether, esters, and the like. Additional ingredients such as sodium meta bisulfite may also be added to the reaction mixture.

A particularly useful dispersant according to the method of the invention is "DARVAN 1" (sodium naphthalene sulfonic acid formaldehyde, a product of R. T. Vanderbilt Co. Inc.). Similar dispersants are commercially available under the tradenames "DEMOL N" (sodium salt of naphthalene sulfonic acid, a product of Kao Chemicals), "DAXAD 11" (sodium salt of polymerized alkyl naphthalene sulfonic acids, a product of W. R. Grace & Co.), and "TAMOL N" (sodium salt of condensed naphthalene sulfonic acid, a product of Rohm and Haas Co.).

The dispersant is suitably employed in the method of the present invention alone or in combination with a surfactant. Useful surfactants are suitably selected from the classes of surfactants known as nonionics, anionics, cationics, and amphoterics (the latter being also commonly referred to as "zwitterionics"). The surfactants are suitably employed singly, or in combinations of two, three, or even four or more surfactants selected from the above-mentioned four classes.

Useful nonionic surfactants include linear alcohol alkoxylates, such as the linear alcohol ethoxylates, ethyoxylated/propoxylated block copolymers, ethyoxylated/propoxylated fatty alcohols, and polyoxyethylene cetyl ethers, and the like. Useful linear alcohol alkoxylates are commercially available, for example, under the registered trademark POLY-TERGENT SL-42, a product of Olin Corporation. If desired, the alcohol alkoxylate is suitably end-capped with a lower alkyl group, and such a product is commercially available as POLY-TERGENT SLF-18, a propylene oxide-capped linear alcohol alkoxylate that is also a product of Olin Corporation, and these end-capped linear alcohol alkoxylates are notably low foaming during use. Also advantageous for use in accordance with the present invention are surfactants within the group commercially available as POLY-TERGENT SLF-18B series surfactants, which are surfactants characterized by enhanced biodegradability (also products of Olin Corporation), being alkene oxide-capped linear alcohol alkoxylates, containing ethylene oxide moieties in the backbone, and suitably also containing at least one propylene oxide moiety in the backbone, as disclosed, for example, in U.S. Pat. Nos. 4,925,587 and 4,898,621.

Other useful nonionic surfactants include one commercially available as NEODOL 91-6, a registered trademark surfactant product of Shell Chemical. This surfactant is a detergent range mixture of $C_9$–$C_{11}$ linear primary alcohol ethoxylates having an average of six moles of ethylene oxide per mole of alcohol. Other useful nonionic surfactants include those containing a linear $C_9$–$C_{11}$ carbon chain and five or six ethylene oxide or propylene oxide groups per molecule.

Useful anionic surfactants include alkyl diphenylether disulfonates, alkyl phenyl ethoxylated phosphate esters, carboxylated linear alcohol alkoxylates, linear alkyl benzene sulfonic acid, diisobutyl sulfosuccinate, and alkyl sulfonates. Useful anionics also include the alkylated diphenyl oxide sulfonates, and their methods of preparation are well-known, as illustrated by the disclosures of U.S. Pat. Nos. 3,264,242; 3,634,272; and 3,945,437, the disclosures of which are all incorporated herein by reference. Commercial methods of preparation of the alkylated diphenyl oxide sulfonates generally do not produce species which are monoalkylated, monosulfonated, dialkylated or disulfonated. The commercially available species typically are predominately (greater than 90 percent) disulfonated and are a mixture of mono- and di-alkylated with the percentage of dialkylation being about 15 to about 25 percent, and the percentage of monoalkylation being about 75 to 85 percent. Most typically, the commercially available species are about 80 percent monoalkylated and 20 percent dialkylated.

Two illustrative commercially available solutions containing alkylated diphenyl oxide sulfonate surfactants are DOWFAX 8390 and DOWFAX 8390A surfactants, trademarked products of The Dow Chemical Company. In each, the alkyl group is predominantly a hexadecyl $C_{16}$ group. These products are suitably employed in a solution fully or partially neutralized with ammonium hydroxide if desired.

An advantageous anionic surfactant is also provided by reacting the above-described alkylated diphenyl oxide sulfonates with a piperazine compound to produce a molar ratio of sulfonate compound to piperazine compound of between about 10:1 and about 1:10, preferably between about 2:1 and about 1:2. Although any piperazine compound can be used for such reaction, preferred compounds include those selected from the group consisting of 1,2-aminoethyl piperazine, 1,4-piperazinediethane sulfonic acid, anhydrous piperazine, hydrated piperazine, and combinations thereof.

Other useful anionics are polycarboxylated alcohol alkoxylates, preferably those selected from acids or organic or inorganic salts of the following: polycarboxylated linear alcohol alkoxylates, polycarboxylated branched alcohol alkoxylates, polycarboxylated cyclic alcohol alkoxylates, and combinations thereof. These polycarboxylated alcohol alkoxylates typically contain at least two succinic acid radicals per molecule. Preferred polycarboxylated alcohol alkoxylates are those having a backbone containing both poly(propylene oxide) and poly(ethylene oxide) blocks, and such preferred polycarboxylated alcohol alkoxylates are readily commercially available, for example, as POLY-TERGENT CS-1, a trademarked surfactant of Olin Corporation. If desired, at least a portion of the acid groups on the polycarboxylated alcohol alkoxylate are neutralized with a base to provide the corresponding salt. Suitable bases include alkali metal hydroxides, alkaline earth metal hydroxides, and metal-free hydroxides, including potassium hydroxide, ammonium hydroxide, calcium hydroxide, magnesium hydroxide, ammonia, mono-, di- and tri-ethanol amines, and combinations thereof. Sodium hydroxide is preferred, and although potassium hydroxide can be employed, it is not preferred. The organic or inorganic base is preferably employed in at least an equimolar amount relative to the number of moles of polycarboxylated alcohol alkoxylated used. The polycarboxylated alcohol may also contain a polycarboxylic acid, for example, polyacrylic acid, along with the starting alcohol alkoxylate and esters of the alkoxylate of the polycarboxylic acid.

Although individually the cationic and the amphoteric surfactants are acceptable for use in the process of the present invention, they may also be used in combination with at least one surfactant from one of the other classes. Illustrative cationics include alkyl triammonium halide, non-linear alkyl dimethyl halide and alkyl dimethyl benzyl ammonium halide-containing surfactants. Illustrative amphoteric surfactants include polyglycol ether derivatives, ethoxylate oxazoline derivatives, lauramidopropyl betaine, and lecithin.

Suitable blends can be employed in the process of the present invention based on various combinations of the above-described surfactants. Such a blend can be any combination of two or more surfactants, between or within the above-described four broad classes of surfactants. Combinations can include blends of: anionic with anionic, anionic with nonionic, anionic with cationic, anionic with amphoteric, cationic with cationic, cationic with amphoteric, nonionic with nonionic, nonionic with amphoteric, and amphoteric with amphoteric. Likewise, ternary and quaternary blends of surfactants by selecting three or four surfactants, respectively, from within or among the above-described classes.

Suitably, any single or combination of two, three or four surfactants from the following illustrative list are suitably employed: (a) nonionics, including alkoxylated linear alcohols (such as POLY-TERGENT SLF-18 surfactant, a product of Olin Corporation), linear alcohol ethoxylates (such as NEODOL 91-8 surfactant, a product of the Shell Corporation), ethoxylated linear alkyl benzene (such as TRITON X-100 surfactant, a product of Union Carbide Corporation), and EO/PO block copolymers (such as POLY-TERGENT E-17A surfactant, a product of Olin Corporation); (b) anionics, including alkyl diphenyl ether disulfonates (such as POLY-TERGENT 2A1 surfactant, a product of Olin Corporation), alkyl phenyl ethoxylated phosphate esters (such as Wayfos M-60 surfactant, a product of Olin Corporation), carboxylated linear alcohol alkoxylates (such as POLY-TERGENT CS-1 surfactant, a product of Olin Corporation), linear alkyl benzene sulfonic acid (such as BIOSOFT S-130 surfactant, a product of Stepan Company), alpha-olefin sulfonates (such as BIO TERG AS-40 surfactant, a product of Stepan Company), dialkyl-sulfosuccinates (such as AROWET SC-75 surfactant, a product of Arol Chemical Products), and alkyl sulfates (such as STEPANOL SLS surfactant, a product of Stepan Company); (c) cationics including alkyl triammonium halides (such as CTAB surfactant, a product of VWR Scientific Inc.), polyoxyethylene cocoamine (such as MAZEEN surfactant, a product of PPG Industries), primary alkyl amines (such as ARMEEN surfactant, a product of Akzo Chemical Co.), dicoco dimethyl ammonium halide (such as JET QUAT surfactant, a product of Jetco Chemical Inc.), di-isodecyl dimethyl ammonium halides (such as AMMONYX K9 surfactant, a product of Stepan Company), and diethyl aminoethyl stearate (such as CERASYNT 303 surfactant, a product of ISP Van Dyke); and, (d) amphoterics, including polyglycol ether derivatives (such as ALBEGAL A surfactant, a product of Ciba-Geigy), ethoxylated oxazolin derivatives (such as ALKATERG T-IV surfactant, a product of Angus Chemicals), lauramide propyl betain (such as LEXAINE C surfactant, a product of Inolex Chemicals), lecithin (such as CANASPERSE surfactant, a product of Can Amoral), disodium cocoamphodiacetate (such as MONATERICS surfactant, a product of Mona Industries), complex fatty amine salt (such as MAFO 13 surfactant, a product of PPG Industries), and cocoamine oxide (such as MACKAMINE CO surfactant, a product of the McIntyre Group Ltd.).

The dispersant or dispersant/surfactant combination is preferably employed in a total amount of between about 0.05 and 10%, more preferably between about 0.1 and 5%, most preferably between about 0.5 and about 1.5% by weight, based on the total weight of the reaction mixture.

The temperature of the reaction may be any temperature which permits precipitation of particles of pyrithione salt. Preferable temperatures for the reaction are in the range of from between about −10 and about 100° C., and more preferably between about 25° C. and about 95° C. A particularly useful working temperature is about 60–70° C.

In the batch preparation of particles, the reactants are combined slowly, preferably over about 30–240 minutes, more preferably from about 35 to about 120 minutes, and most preferably from about 40 to about 90 minutes.

During the reaction, sonic energy is applied to the reaction mixture to form a highly uniform suspension of non-agglomerated particles. The sonic energy preferably has a frequency of from about 20 Hz to about 250,000 Hz (250 kHz), more preferably from about 5 kHz to about 105 kHz, and most preferably from about 16 kHz to about 20 kHz. Combinations of frequencies may also be used, depending on the configuration of the particular sonication apparatus. The energy level output that results from the sonic energy applied to the reaction mixture is preferably in the range from about 20 to about 5000 Watts, more preferably from about 100 to about 1000 Watts, and most preferably from about 400 to about 600 Watts. An example of a suitable sonication device that is useful according to the method of the invention is a Nearfield NAP Model 3606 acoustical processor (available commercially from Advanced Sonic Processing Systems, Woodbury, Conn.), although any sonication device may be employed in the method of the invention.

It will be noted that the sound levels that could be produced using the levels of sonic energy discussed above can exceed 100 decibels (dB) and potentially reach levels as high as 140 dB. In order to avoid hearing impairment, proper safety and sound abatement procedures should be undertaken when decibel levels are greater than about 80 dB.

Preferably, in the batch process, sonic energy is applied to the reaction mixture through a climate probe that is placed in direct contact with the reactants. Other methods of applying sonic energy are also feasible, such as a pipe which carries the sonic energy to the reaction vessel, or a chamber lined with sonic energy transducers. The latter method is particularly useful in the continuous manufacture of particles as described in more detail below.

Particles of pyrithione salts made according to the method of the invention preferably range in size from about 0.1 to about 50 microns, more preferably from about 0.1 to about 15 microns, and most preferably from about 0.1 to 5 microns.

The suspensions of non-agglomerated particles made according to the method of the invention may be produced in a single batch, or continuously. As described in more detail below, the single batch process generally involves placing all the reactants in a reaction vessel and applying sonic energy to the contents of the reaction vessel. In an alternative embodiment, the batch process may involve placing all but one of the reactants in the vessel, and adding the single remaining reactant slowly while sonic energy is applied to the reaction mixture. In an alternative embodiment, the method of the invention may be practiced in a "continuous flow" mode as shown in FIG. 1 to rapidly and continuously form a uniform, well-dispersed suspension of particles.

As shown in FIG. 1, the "continuous flow" mode of the method of the invention utilizes a continuous flow reaction device 10 which includes a reaction chamber 12 which allows for continuous mixing of the reactants. Input conduits 14, 16 allow the reactants to enter the reaction chamber 12, while a collection conduit 18 collects the product produced from the continuous reaction. In one embodiment, one reactant input pipe 14 can carry an aqueous solution of sodium pyrithione and a surfactant, and another reactant input pipe 16 can carry an aqueous solution of zinc sulfate or zinc chloride.

The reactor has sonic energy transducer assemblies 20 and 22 located at opposite sides of the reaction chamber 12. The transducer assemblies 20 and 22 have respective housings 24 and 26 containing sonic energy transducers 28 and 30 of which 28A–28C and 30A–30C, respectively, are shown. The sonic energy transducers are arranged in pairs (i.e., 28A and 30A, 28B and 30B, and 28C and 30C). Each transducer 28 applies energy to a first wall or side 32 of the reaction chamber 12 while directly opposite an associated transducer 30 applies energy to the second wall 34.

In the illustrated embodiment, the input pipe 14 enters an upstream end of the reaction chamber 12 along the side 32. The input pipe 16 enters downstream of the input pipe 14 along a wall 36 transverse to the walls 32 and 34. The inlet from the reactant input pipe 16 to the reaction chamber 12 is positioned to introduce the solution from pipe 16 to that from pipe 14 at a location proximate the first pair of transducers (28A and 30A). As the combined reactants flow through reaction chamber 12, a sonic energy is applied by the sonic energy transducers 28 and 30, and are arranged to expose nearly the entire length of the reaction chamber 12 with sonic energy as the reactants move through the reaction chamber 12, toward the collection conduit 18. Optionally, there may be multiple input conduits 16 having inlets to the reaction chamber 12 at multiple longitudinal locations therealong. Also, such input conduits 16 may be located on the side (not shown) opposite the side 36 or along the sides 32 and 34. Additional apparatus such as a heat exchanger (not shown) may also be included along the length of the reaction chamber 12 to maintain the proper temperature during the reaction.

The two streams of reactants contained within the reactant input conduits 14 and 16 converge at one end of the array of transducer pairs, and solid precipitated particles are produced. As the reactants converge, and advantageously at the point of contact of the reactants, sonic energy is applied to the reaction mixture from the sonic energy transducers. Without wishing to be bound to any particular theory, it is believed that the sonic energy, being applied at the point of contact of the reactants with each other, causes intimate mixing of the reactants in a short time period, and increases the likelihood that the reaction will go rapidly to its desired completion. Preferably, the sonic energy transducers of the two assemblies 20, 22 emit different frequencies of sonic energy, e.g., 16 kHz and 20 kHz. The application of sonic energy from the sonic energy transducers results in production of a uniform suspension of individual, non-agglomerated particles in the aqueous medium, each particle having sizes from 0.1 to about 30 microns.

Suitable flow rates for the continuous process of the present invention range from about 0.1 to about 350 gallons per minute, more preferably from about 5 to about 100 gallons per minute, and most preferably from about 15 to about 50 gallons per minute.

It will be appreciated that while the examples show suspensions of pyrithione particles being produced according to the method of the invention, any suspension of small particles may be made by the method by proper choice of reactants and levels of applied sonic energy. In addition, the average particle sizes of the particles made according to the method of the reaction may vary from small (e.g., 0.1–5 microns) to large (e.g., 10–30 microns).

The uniform, well-dispersed suspension of non-agglomerated particles made according to the method of the invention is useful in the production of personal care products (e.g., shampoos, soaps, etc.), cleaning products, paints, coatings, foodstuffs, fertilizers, pool chemicals, and the like. Moreover, when practiced in a continuous operation mode, the method of the invention permits generation of a greater quantity of uniform, well-disperse, non-agglomerated particles in a suspension in a short amount of time as compared with conventional batch processing. The high throughput of the method of the invention permits increased efficiency, decreased cost, and greater productivity of the production plant.

It will also be appreciated that the method of the present invention also provides an efficient procedure to mix various liquids, for example, to form an emulsion. In one embodiment, an organic liquid and an aqueous liquid are combined according to the method of the invention. Application of sonic energy results in rapid and uniform production of an emulsion of the two reactants by producing a well-dispersed mixture of very small vesicles of aqueous liquid and organic liquid.

The following examples are intended to illustrate, but in no way limit the scope of the present invention. All parts and percentages are by weight and all temperatures are in degrees Celsius unless explicitly stated otherwise.

EXAMPLES

Example 1

Continuous Preparation of Zinc Pyrithione

A 12.0% aqueous solution of the sodium salt of 2-mercaptopyridine N-oxide (sodium pyrithione) containing 0.5% DARVAN 1 and 0.15% sodium meta bisulfite was heated to 58 to 65° C. This solution was fed continuously into a laboratory scale Nearfield Acoustical Processor ("NAP" Model NAP-1808) available commercially from Advanced Sonic Processing Systems, Woodbury, Conn.) at a rate of about 156 grams per minute. A second solution of 20% zinc sulfate at room temperature was fed into the acoustical processor at a rate of about 56 grams per minute to achieve a stoichiometric reaction with the sodium pyrithione solution. As the reactants moved through the acoustical unit, sonic energy having 16 kHz and 20 kHz and a power level of about 500 watts was applied to mix the reactants as they form the zinc pyrithione product. The resulting solid particles were isolated by filtration. After filtration, the particles were washed with cold water until free of contaminating salt as measured by conductivity.

Analysis of the resulting cake of material indicated that zinc pyrithione particles represented about 35–55% by weight of the total wet material. An optional filtration step using a Larox filtration device could decrease the amount of water and increase the amount of pyrithione in the cake to about 75–80% by weight. The cake was then converted to an aqueous dispersion of from about 5 to 65% by weight, more preferably from about 10 to about 50% by weight, and most preferably from about 20 to 48% by weight. Optional additives such as surfactants may be included in the aqueous dispersion to maintain the dispersion during storage. The aqueous dispersion may also be optionally sterilized before bottling.

The particles were analyzed on a Horiba 910 Particle Size Analyzer and by microscopy and showed a uniform, well-dispersed suspension of non-agglomerated zinc pyrithione particles.

Example 2

Continuous Preparation of Zinc Pyrithione

The same procedure and amounts of materials as described in Example 1 above were used. However, the flow rate of sodium pyrithione/DARVAN 1/sodium meta bisulfite solution was 78 grams per minute, and the flow rate of the zinc sulfate solution was 28 grams per minute. Sonication, filtration and analysis of the particles was conducted as described in Example 1.

Analysis of the resulting cake of material indicated that zinc pyrithione particles represented about 35–55% by weight of the total wet material. An optional filtration step using a Larox filtration device could decrease the amount of water and increase the amount of pyrithione in the cake to about 75–80% by weight. The cake was then converted to an aqueous dispersion of from about 5 to 65% by weight, more preferably from about 10 to about 50% by weight, and most preferably from about 20 to 48% by weight. Optional additives such as surfactants may be included in the aqueous dispersion to maintain the dispersion during storage. The aqueous dispersion may also be optionally sterilized before bottling.

The particles were analyzed on a Horiba 910 Particle Size Analyzer and by microscopy and showed a uniform, well-dispersed suspension of non-agglomerated zinc pyrithione particles.

Example 3

Continuous Preparation of Zinc Pyrithione

A. Laboratory Scale Production

Figure 4:
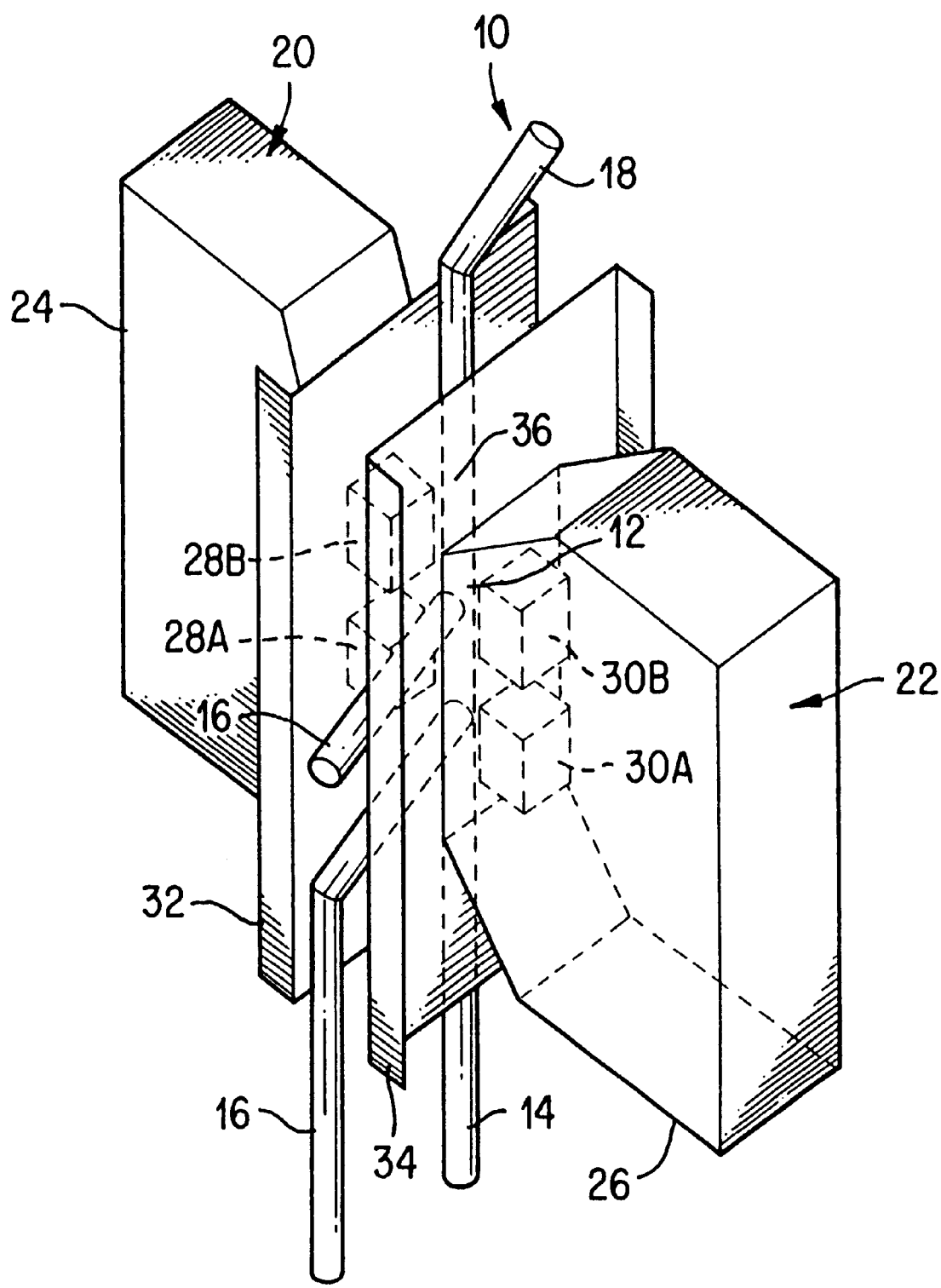
FIG. 4 is a perspective view of one embodiment of reactor design for the continuous process of the invention.

The same procedure and amounts of materials as described in Example 1 above are used. However, the flow rate of sodium pyrithione/DARVAN 1/sodium meta bisulfite solution through the NAP-1808-TC reactor, modified to include input conduits 14 and 16 as shown in FIG. 4, was 312 grams per minute and the flow rate of the zinc sulfate solution was 112 grams. Sonication, filtration and analysis of the particles was conducted as described in Example 1.

b. Pilot Plant Scale Production

The same procedure and amounts of materials as described in Example 1 above are used. However, the flow rate of sodium pyrithione/DARVAN 1/sodium meta bisulfite solution was 65 lbs/fed into NAP 3606 model/also, and the flow rate of the zinc sulfate solution was 20 lbs/min per minute NAP 36-06. Sonication, filtration and analysis of the particles was conducted as described in Example 1.

Analysis of the resulting cake of material indicated that zinc pyrithione particles represented about 35–55% by weight of the total wet material. An optional filtration step using a Larox filtration device could decrease the amount of water and increase the amount of pyrithione in the cake to about 75–80% by weight. The cake was then converted to an aqueous dispersion of from about 5 to 65% by weight, more preferably from about 10 to about 50% by weight, and most preferably from about 20 to 48% by weight. Optional additives such as surfactants may be included in the aqueous dispersion to maintain the dispersion during storage. The aqueous dispersion may also be optionally sterilized before bottling.

The particles were analyzed on a Horiba 910 Particle Size Analyzer and by microscopy and showed a uniform, well-dispersed suspension of non-agglomerated zinc pyrithione particles. Scanning electron microscopy ("SEM") analysis of the particles showed them to be of hexagonal shape with sharp edges and corners. The particles were essentially free of "terracing" of a mica-like character that tend to be found using conventional batch processes in the absence of sonication.

Example 4

Batch Preparation of Zinc Pyrithione 500.0 g of 12.0% aqueous solution of the sodium salt of 2-mercaptopyridine N-oxide (sodium pyrithione) was charged to a 1 liter round bottom 4 neck glass reactor. A sonication probe was placed inside the reactor through the wide center neck. The tip of the sonication probe was between about 0.5–1 inch away from the bottom of the reactor. The power to the sonication probe was approximately 30–80 watts and resulted in a sonication frequency of about 10 kHz. 1.5 g of DARVAN 1 and 0.75 g of sodium meta bisulfite were added to the reactor, and the reactor was heated to either 55° C., 72° C. or 92° C. depending on the desired particle size. 185.0 g of a 20.0% (w:w) zinc sulfate solution which was preheated to 78–90° C. was added subsurface to the reactor over 40 minutes. During the reaction, solid particles of zinc pyrithione were produced.

Once the reaction was complete, sonication continued for an additional 30 minutes, and the reactor was allowed to cool to about 55° C. The cooling process was not expedited by any cooling devices. The resulting zinc pyrithione suspension was extremely fluid and could be isolated by filtration with a Buchner funnel using Whatman No. 5 filter paper. Isolation by centrifugation was also possible. After filtration or centrifugation, the particles were washed with cold water until free of contaminating salt as measured by conductivity.

Analysis of the resulting cake of material indicated that zinc pyrithione particles represented about 35–55% by weight of the total wet material. An optional filtration step using a Larox filtration device could decrease the amount of water and increase the amount of pyrithione in the cake to about 75–80% by weight.

The cake was then suitably converted to an aqueous dispersion of from about 5 to 65% by weight, more preferably from about 10 to about 50% by weight, and most preferably from about 20 to 48% by weight. Optional additives such as surfactants may be included in the aqueous dispersion to maintain the dispersion during storage. The aqueous dispersion may also be optionally sterilized before bottling.

The particles were analyzed on a Horiba 910 Particle Size Analyzer and by microscopy and showed a uniform, well-dispersed suspension of non-agglomerated zinc pyrithione particles.

Example 5

Batch Preparation of Zinc Pyrithione

The same procedure and amounts of materials as described in Example 4 above were used with the exception of replacing DARVAN 1 with a combination of three surfactants. The surfactant combination was prepared by mixing 7.5 gm of anionic POLY-TERGENT 2A-1L, 7.5 gm of anionic POLY-TERGENT CS-1 and 15 gm of cationic trimethylammonium chloride (also known as CTAC).

This pre-mixed surfactant blend was added to the sodium pyrithione contained in the reactor with ongoing sonication for 10 minutes to insure proper mixing. The reactor was then heated to the desired temperature over 10–30 minutes, and precipitation, cooling, isolation (filtration or centrifugation) and washing were as described in Example 4.

Analysis of the resulting cake of material indicated that zinc pyrithione particles represented about 35–55% by weight of the total wet material.

An optional filtration step using a Larox filtration device, Larox Corp. Columbus, Md., could decrease the amount of water and increase the amount of pyrithione in the cake to about 75–80% by weight. The cake was then suitably converted to an aqueous dispersion of from about 5 to 65% by weight, more preferably from about 10 to about 50% by weight, and most preferably from about 20 to 48% by weight. Optional additives such as surfactants may be included in the aqueous dispersion to maintain the dispersion during storage. The aqueous dispersion may also be optionally sterilized before bottling.

The particles were analyzed on a Horiba 910 Particle Size Analyzer and by microscopy and showed a uniform, well-dispersed suspension of non-agglomerated zinc pyrithione particles.

Example 6

Batch Preparation of Zinc Pyrithione

The same procedure as described above for Example 4 was used here except that 500 g of a 22.4% sodium pyrithione solution was used instead of 500 g of a 12% sodium pyrithione solution, and 103 g of a 50% zinc chloride solution was used instead of 185 g of a 20% zinc sulfate solution. The amount of other additives, the way they were added, temperatures, filtration, centrifuge and washing the cake were the same as Example 4. Precipitation, cooling, isolation (filtration or centrifugation) and washing were all conducted as described in Example 4.

Analysis of the resulting cake of material indicated that zinc pyrithione particles represented about 35–55% by weight of the total wet material. An optional filtration step using a Larox filtration device could decrease the amount of water and increase the amount of pyrithione in the cake to about 75–80% by weight.

The cake was then suitably converted to an aqueous dispersion of from about 5 to 65% by weight, more preferably from about 10 to about 50% by weight, and most preferably from about 20 to 48% by weight. Optional additives such as surfactants may be included in the aqueous dispersion to maintain the dispersion during storage. The aqueous dispersion may also be optionally sterilized before bottling.

The particles were analyzed on a Horiba 910 Particle Size Analyzer and by microscopy and showed a uniform, well-dispersed suspension of non-agglomerated zinc pyrithione particles.

Example 7

Antidandruff Shampoo Formulation I (Proposed Example)

An antidandruff shampoo composition is made using non-agglomerated particles of zinc pyrithione made as described in Examples 1–6 above in combination with the following ingredients:

| Component A: | |
|---|---|
| Water | 41.0% |
| Magnesium aluminum silicate | 1.0% |
| Hydroxypropyl methylcellulose | 0.8% |
| Component B: | |
| Zinc Pyrithione (25% aqueous dispersion) | 4.0% |
| Component C: | |
| Cocamide DEA | 1.0% |
| Component D: | |
| Triethanolamine lauryl sulfate, 40% | 40.0% |
| Triethanolamine, 99% | 3.2% |
| FD&C Blue No. 1 (0.2%) | 1.5% |
| FD&C Yellow No. 5 (0.1%) | 0.5% |
| Fragrance | q.s. |

The antidandruff shampoo composition was made as follows:

Component A was prepared by heating water to 70° C. and dissolving the other two components with stirring (about 1500 rpm). Component B was added, and stirring continued for 5 minutes. Stirring speed was reduce stirring to ~300 RPM. Component C was melted in a separate container, and added to the A/B mixture. The heat was removed and component D was added while the mixture cooled.

Example 8

Antidandruff Shampoo Formulation II (Proposed Example)

Another antidandruff shampoo composition is made using zinc pyrithione made as described in Examples 1–3 in combination with the following ingredients:

| Component A: | |
|---|---|
| Deionized water | 76.0% |
| Ammonium lauryl sulfate | 15.0% |
| Cocamide DEA | 2.0% |
| Component B: | |
| Di (hydrogenated) tallow phthalic acid amide | 5.0% |
| Zinc Pyrithione (25% aqueous dispersion) | 4.0% |
| Component C: | |
| Preservative | q.s. |
| Component D: | |
| Citric Acid, 50% aq. Solution, OR Sodium hydroxide, 50% aqueous solution | q.s. |
| Component E: | |
| Ammonium chloride | q.s. |

The antidandruff shampoo composition was made as follows:

In separate containers, components A and B were each mixed well. Component A was heated to 165–170° F. and component B was added. The mixture was stirred for 30 minutes. The mixture was then cooled to 120° F., and component C was added. The pH of the resulting mixture was adjusted to 5.0–6.2 with component D, and the viscosity was adjusted with component E.

Example 9

Antidandruff Shampoo with Conditioner I
(Proposed Example)

An antidandruff shampoo and conditioner composition is made using zinc pyrithione made as described in Examples 1–3 in combination with the following ingredients:

| Component A: | |
|---|---|
| Deionized Water | 77.0% |
| Ammonium lauryl sulfate | 20.0% |
| Cocamide DEA | 2.0% |
| Component B: | |
| Di (hydrogenated) tallow phthalic acid amide | 4.0% |
| Zinc Pyrithione (25% aqueous dispersion) | 4.0% |
| Dimethicone, 12,000 cps | 0.5% |
| Component C: | |
| Preservative | q.s. |
| Component D: | |
| Citric acid, 50% aqueous solution, OR Sodium hydroxide, 50% aqueous solution | q.s. |
| Component E: | |
| Ammonium chloride | q.s. |

The antidandruff shampoo and conditioner composition was made as follows:

In separate containers, components A and B were each mixed well. Component A was heated to 165–170° F. and component B was added. The mixture was stirred for 30 minutes. The mixture was then cooled to 120° F., and component C was added. The pH of the resulting mixture was adjusted to 5.0–6.2 with component D, and the viscosity was adjusted with component E.

Example 10

Antidandruff Shampoo with Conditioner II
(Proposed Example)

Another antidandruff shampoo and conditioner composition is made using zinc pyrithione made as described in Examples 1–3 in combination with the following ingredients:

| Component A: | |
|---|---|
| Deionized water | 21.75% |
| Guar hydroxypropyl trimonium chloride | 0.30% |
| Magnesium Aluminum Silicate | 0.70% |
| Zinc Pyrithione (25% aqueous dispersion) | 4.0% |
| Component B: | |
| Sodium laureth sulfate | 30.0% |
| Ammonium xylene sulfonate, 40% aq. | 02.0% |
| Component C: | |
| Tricetylammonium chloride | 0.50% |
| Cetyl alcohol NF | 0.40% |
| Stearyl alcohol | 0.40% |
| Glycol distearate | 2.00% |
| Component D: | |
| Cocamide MEA | 1.70% |
| Ammonium lauryl sulfate | 36.00% |
| Component E: | |
| Preservative | 0.05% |
| Fragrance and dye | q.s. |
| Component F | |
| Citric acid, 25% aqueous solution | q.s. |

The antidandruff shampoo and conditioner composition was made as follows:

Component A was prepared by heating water to 50° C. and dispersing the guar hydroxypropyl trimonium chloride and the magnesium aluminum silicate with rapid agitation. The zinc pyrithione dispersion was added to this combination with stirring. The pH of component A was adjusted to 4.5–5.0 with component F. Both components of B were slowly added to component A, mixing well. The pH of the mixture was adjusted to 5.7–6.3 with component F. In a separate container, component C was heated to 70–75° C. The A/B mixture was heated to 70–75° C. and blend with component C, mixing well. Both components of D were added to the hot mixture, and stirred well. The pH of the mixture was adjusted to 5.7–6.3 with component F. The mixture was cooled to 40–45° C., and component E was added with stirring. If desired, adding 0.05–1% sodium chloride can increase the viscosity of the product.

Example 11

"Extra Body" Antidandruff Shampoo (Proposed Example)

An "extra body" antidandruff shampoo and conditioner composition is made using zinc pyrithione made as described in Examples 1–3 in combination with the following ingredients:

| Component A: | |
|---|---|
| Deionized Water | 62.6% |
| Zinc Pyrithione (25% aqueous dispersion) | 4.0% |
| Component B: | |
| Methyl Paraben | 0.30% |
| Propyl Paraben | 0.10% |
| Propylene Glycol | 0.50% |
| Sodium Chloride | 0.50% |
| Component C: | |
| Triethanolamine lauryl sulfate | 20.0% |
| Cocamide MEA | 4.0% |
| Ethylene glycol distearate | 7.0% |
| Component D: | |
| Cocodimonium hydrolyzed animal protein | 1.00% |
| Component E: | |
| FD&C Blue No. 1 | q.s. |
| Component F: | |
| Citric Acid, 50% aqueous solution | q.s. |

The antidandruff shampoo and conditioner composition was made as follows:

Component A was heated to 70° C. The ingredients of component B were added with good stirring until dissolved. The ingredients of component C were added to the mixture sequentially, and heated with mixing to 75° C. The mixture was cooled with stirring to 40° C., and components D and E were added with stirring. The pH of the final composition was adjusted to 4.7 with component F.

Although the invention has been shown and described with respect to illustrative embodiments thereof, it should be appreciated that the foregoing and various other changes, omissions and additions in the form and detail thereof may be made without departing from the spirit and scope of the invention as delineated in the claims. All patents and patent applications mentioned are herein incorporated by reference in their entirety.

What is claimed is:

1. A hexagonal shaped particle of zinc pyrithione characterized by sharp particle corners and straight particle edges, said particle being produced by reacting pyrithione or a water-soluble salt of pyrithione and a water-soluble polyvalent metal salt in an aqueous medium and in the presence of a dispersing additive to produce particles of pyrithione salts, wherein sonic energy is applied to said aqueous medium during said reacting step to produce a suspension of non-agglomerated pyrithione salt particles, said non-agglomerated pyrithione salt particles having a hexagonal shape and median size of from about 0.1 to about 50 micros wherein said dispersing additive is carboxymethyl cellulose.

2. An antidandruff shampoo comprising a suspension, emulsion, or dispersion of non-agglomerated particles of pyrithione salts made by reacting pyrithione or a water-soluble salt of pyrithione and a water-soluble polyvalent metal salt in an aqueous medium and in the presence of a dispersing additive to produce particles of pyrithione salts, wherein sonic energy is applied to said aqueous medium during said reacting step to produce said suspension emulsion or dispersion of non-agglomerated pyrithione salt particles, said non-agglomerated pyrithione salt particles having a median size of from about 0.1 to about 50 microns wherein said dispersing additive is carboxymethyl cellulose.

* * * * *

UNITED STATES PATENT AND TRADEMARK OFFICE
CERTIFICATE OF CORRECTION

PATENT NO. : 6,682,724 B2
DATED : January 27, 2004
INVENTOR(S) : Saeed H. Mohseni and John J. Jardas It is certified that error appears in the above-identified patent and that said Letters Patent is hereby corrected as shown below:

Column 20,
Line 19, replace the word "micros" with the word -- microns --.

Signed and Sealed this

Seventh Day of September, 2004

JON W. DUDAS
*Director of the United States Patent and Trademark Office*